United States Patent
Kim

(10) Patent No.: US 10,438,357 B2
(45) Date of Patent: Oct. 8, 2019

(54) INTERACTIVE IMAGE SEGMENTING APPARATUS AND METHOD

(71) Applicant: Samsung Electronics Co., Ltd., Suwon-si (KR)

(72) Inventor: Won Sik Kim, Gunpo-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 14/969,152

(22) Filed: Dec. 15, 2015

(65) Prior Publication Data

US 2016/0171709 A1  Jun. 16, 2016

(30) Foreign Application Priority Data

Dec. 15, 2014  (KR) .......................... 10-2014-0180640

(51) Int. Cl.

| G06K 9/34 | (2006.01) |
|---|---|
| G06T 7/11 | (2017.01) |
| G06T 11/20 | (2006.01) |
| G06K 9/62 | (2006.01) |
| G06T 7/12 | (2017.01) |
| G16H 30/40 | (2018.01) |

(52) U.S. Cl.
CPC .............. *G06T 7/11* (2017.01); *G06K 9/6207* (2013.01); *G06T 7/12* (2017.01); *G06T 11/203* (2013.01); *G16H 30/40* (2018.01); *G06T 2207/20104* (2013.01); *G06T 2207/20116* (2013.01); *G06T 2207/20161* (2013.01)

(58) Field of Classification Search
None
See application file for complete search history.

(56) References Cited

U.S. PATENT DOCUMENTS

| 5,754,709 A * | 5/1998 | Moriya .................... G06T 7/12 |
|---|---|---|
| | | 358/461 |
| 5,926,568 A * | 7/1999 | Chaney ................ G06K 9/6206 |
| | | 382/128 |
| 6,256,411 B1 * | 7/2001 | Iida ..................... H04N 1/00795 |
| | | 358/486 |
| 7,079,674 B2 * | 7/2006 | Paragios ................. G06T 7/215 |
| | | 382/128 |

(Continued)

OTHER PUBLICATIONS

T. Chan, et al., "Active Contours Without Edges," IEEE Transactions on Image Processing, vol. 10, No. 2, Feb. 2001, pp. 266-277.

(Continued)

*Primary Examiner* — Feng Niu
(74) *Attorney, Agent, or Firm* — Jefferson IP Law, LLP

(57) ABSTRACT

An interactive image segmenting apparatus and method are provided. The image segmenting apparatus and corresponding method include a boundary detector, a condition generator, and a boundary modifier. The boundary detector is configured to detect a boundary from an image using an image segmentation process. The feedback receiver is configured to receive information about the detected boundary. The condition generator is configured to generate a constraint for the image segmentation process based on the information. The boundary modifier is configured to modify the detected boundary by applying the generated constraint to the image segmentation process.

20 Claims, 13 Drawing Sheets

(56) References Cited

U.S. PATENT DOCUMENTS

| | | | |
|---|---|---|---|
| 7,245,766 B2* | 7/2007 | Brown | G06K 9/6207 382/199 |
| 7,277,582 B2 | 10/2007 | Paragios | |
| 7,400,757 B2* | 7/2008 | Jolly | A61B 5/055 382/131 |
| 7,831,081 B2* | 11/2010 | Li | A61B 8/12 128/922 |
| 8,391,603 B2* | 3/2013 | Tizhoosh | G06K 9/6253 382/128 |
| 8,577,115 B2* | 11/2013 | Gering | G06T 7/174 382/132 |
| 8,582,550 B2* | 11/2013 | Sun | H04W 72/1215 370/346 |
| 8,620,040 B2* | 12/2013 | Grosskopf | A61B 6/466 382/128 |
| 2003/0053667 A1* | 3/2003 | Paragios | G06T 7/215 382/128 |
| 2005/0232485 A1* | 10/2005 | Brown | G06K 9/6207 382/173 |
| 2007/0036404 A1* | 2/2007 | Li | A61B 8/12 382/128 |
| 2009/0226060 A1* | 9/2009 | Gering | G06T 7/174 382/128 |
| 2010/0067424 A1* | 3/2010 | Sun | H04W 72/1215 370/311 |
| 2010/0322489 A1* | 12/2010 | Tizhoosh | G06K 9/6253 382/128 |
| 2013/0050239 A1 | 2/2013 | Karssemeijer et al. | |

OTHER PUBLICATIONS

P-O. Persson, "The Level Set Method," Lecture Notes, MIT 16.920J/2.097J/6.339J Numerical Methods for Partial Differential Equations, Mar. 7, 2005, pp. 1-7.

* cited by examiner

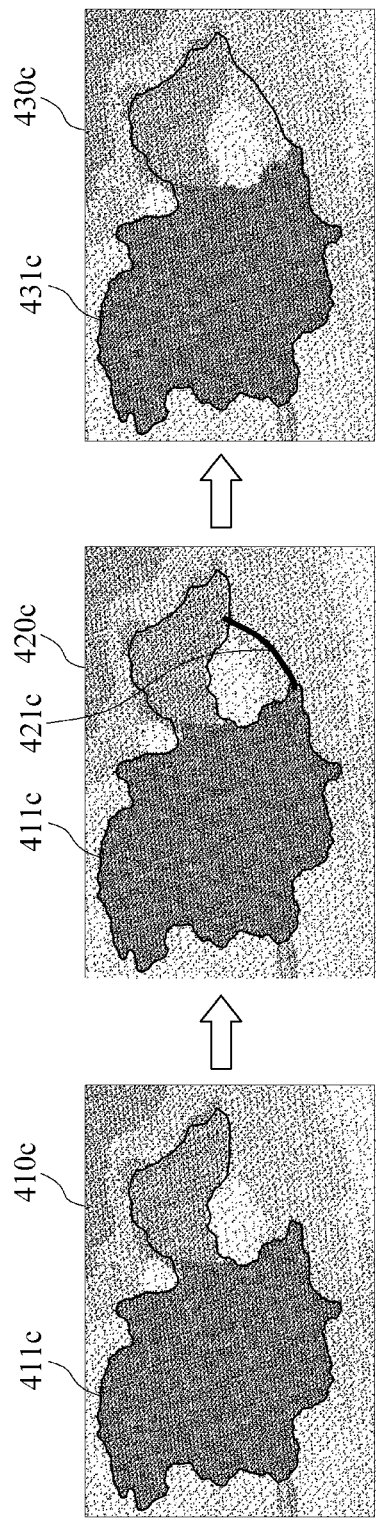

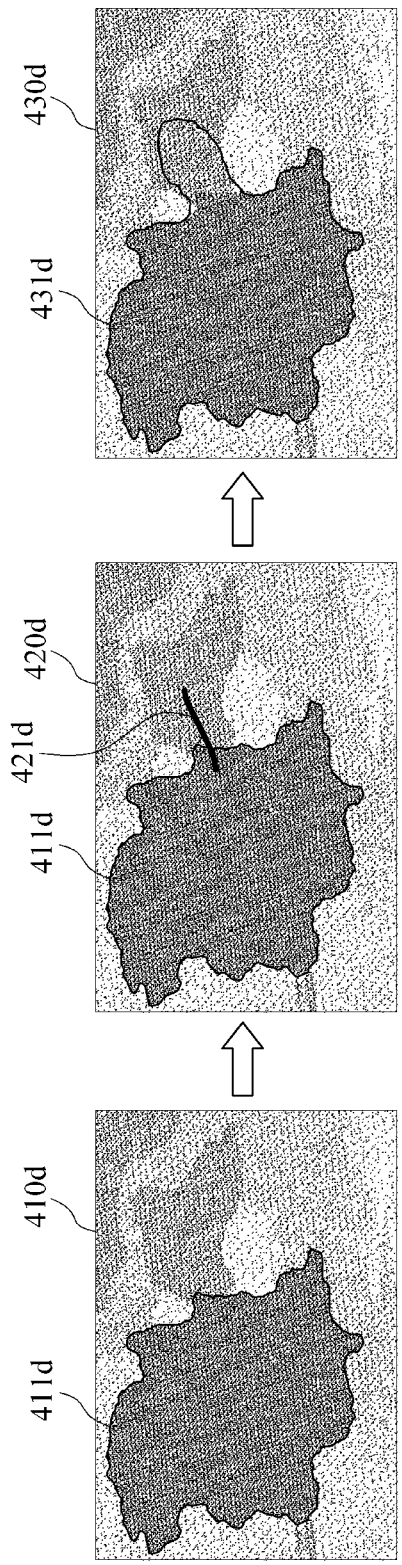

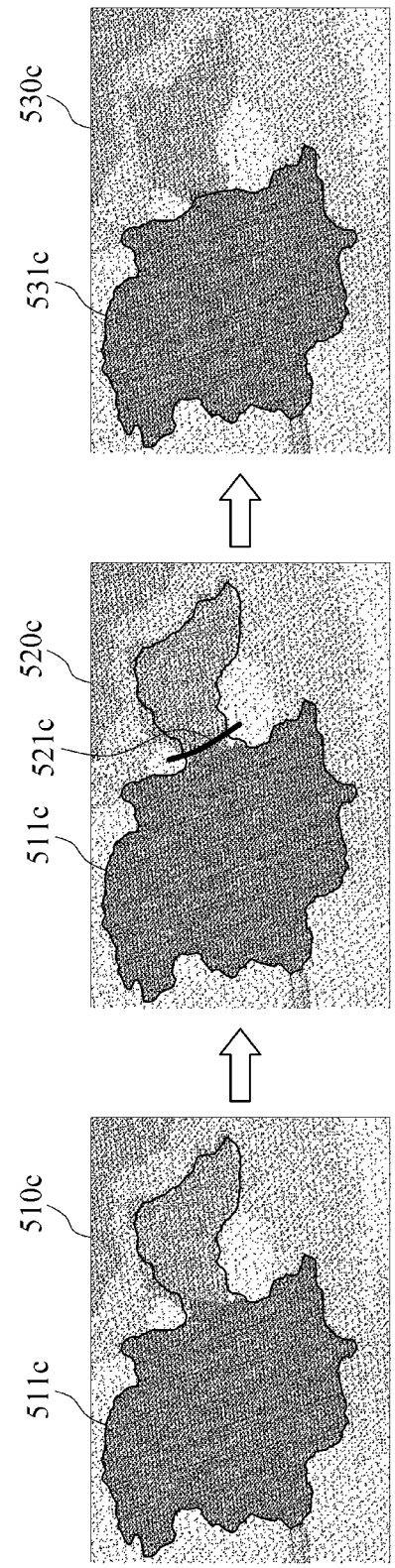

INTERACTIVE IMAGE SEGMENTING APPARATUS AND METHOD

CROSS-REFERENCE TO RELATED APPLICATION(S)

This application claims the benefit under 35 USC 119(a) of Korean Patent Application No. 10-2014-0180640, filed on Dec. 15, 2014, in the Korean Intellectual Property Office, the entire disclosure of which is incorporated herein by reference for all purposes.

BACKGROUND

1. Field

The following description relates to a technology for image segmentation, and more particularly to an interactive image segmenting apparatus and method.

2. Description of Related Art

Generally, information on a contour of a region of interest (ROI) within a medical image is crucial in helping a Computer Aided Diagnosis (CAD) system to obtain an accurate diagnostic result. That is, if a precise contour is drawn for an ROI, such as a lesion region, a correct feature value of the ROI may be extracted. By using the extracted feature value, it is possible to precisely classify the ROI as benign or malignant, thereby enhancing the accuracy of the diagnosis.

However, a user feedback is required because contours provided by a general CAD system are not always precise. Thus, what is required is a technology that improves the accuracy of image segmentation immediately after the user inputs a feedback in an intuitive and convenient way.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with an embodiment, an image segmenting apparatus, including a boundary detector configured to detect a boundary from an image using an image segmentation process; a feedback receiver configured to receive information about the detected boundary; a condition generator configured to generate a constraint for the image segmentation process based on the information; and a boundary modifier configured to modify the detected boundary by applying the generated constraint to the image segmentation process.

The image segmentation process may be a level set process.

The condition generator may be further configured to determine whether the information comprising a user feedback is a boundary expanding feedback or a boundary reducing feedback, and to generate the constraint according to a result of the determination.

The condition generator may be further configured to determine that the user feedback is the boundary expanding feedback when the user feedback comprises one of marking a dot outside the detected boundary, drawing a line outside the detected boundary, drawing a line starting and ending inside the detected boundary and passing outside the detected boundary, or drawing a line starting inside the detected boundary but ending outside the detected boundary.

The condition generator may be further configured to determine that the user feedback is the boundary reducing feedback when the user feedback comprises one of marking a dot inside the detected boundary, drawing a line inside the detected boundary, drawing a line starting and ending outside the detected boundary and passing inside the detected boundary, or drawing a line starting outside the detected boundary but ending inside the detected boundary.

The condition generator may be further configured to include a boundary divider configured to divide, based on a user feedback, the detected boundary into a boundary to be fixed and a boundary to be modified; an image divider configured to divide, based on the division of the detected boundary by the boundary divider, the image into a region to be fixed, a region to be unconditionally modified, and a region to be conditionally modified, and a constraint generator configured to generate a constraint, where the constraint may include sub-constraints to be applied to each of the regions.

The boundary divider may be further configured to calculate a distance between the detected boundary and an annotation marked by the information comprising a user feedback, and divide, based on the calculated distance, the detected boundary into a boundary to be fixed and a boundary to be modified.

The image divider may be further configured to divide the image by determining that a region including the boundary to be fixed is a region to be fixed, that a region including the annotation marked by the information comprising a user feedback is a region to be unconditionally modified, and that the remainder of the image is a region to be conditionally modified.

The constraint generator may be further configured to generate a first sub-constraint for the region to be fixed, a second sub-constraint for the region to be unconditionally modified, and a third sub-constraint for the region to be conditionally modified. Additionally, the boundary modifier may be further configured to modify a first portion of the detected boundary within the region to be fixed by applying the first sub-constraint to the image segmentation process, to modify a second portion of the detected boundary within the region to be unconditionally modified by applying the second sub-constraint to the image segmentation process, and to modify a third portion of the detected boundary within the region to be conditionally modified by applying the third sub-constraint to the image segmentation process.

The boundary divider may be further configured to calculate a distance between the detected boundary and an annotation marked by the user feedback, and to determine that N % of the detected boundary closest to the annotation is the boundary to be modified and the remainder of the detected boundary is the boundary to be fixed.

N may be a constant that has been set in advance according to performance or usage of the image segmenting apparatus, or may be a variable that depends on a context of the user feedback.

In another general aspect, there is provided an image segmenting method including detecting a boundary from an image using an image segmentation process, receiving information about the detected boundary, generating a constraint for the image segmentation process based on the information, and modifying the detected boundary by applying the generated constraint to the image segmentation process.

The image segmentation process may be a level set process.

The generating of a constraint may include determining whether the information comprising a user feedback is a boundary expanding feedback or a boundary reducing feedback, and generating the constraint according to a result of the determination.

The determining whether the user feedback is a boundary expanding feedback or a boundary reducing feedback may include determining that the user feedback is a boundary expanding feedback when the user feedback includes one of marking a dot outside the detected boundary, drawing a line outside the detected boundary, drawing a line starting and ending inside the detected boundary and passing outside the detected boundary, or drawing a line starting inside the detected boundary but ending outside the detected boundary.

The determining whether the user feedback is a boundary expanding feedback or a boundary reducing feedback may include determining that the user feedback is a boundary reducing feedback when the user feedback is one of marking a dot inside the detected boundary, drawing a line in the detected boundary, drawing a line starting and ending outside the detected boundary and passing inside the detected boundary, or drawing a line starting outside the detected boundary but ending inside the detected boundary.

The generating of a constraint may include dividing the detected boundary, based on the user feedback, into a boundary to be fixed and a boundary to be modified; dividing the image, based on the division of the detected boundary, into a region to be fixed, a region to be unconditionally modified, and a region to be conditionally modified; and generating a constraint, where the constraint may comprise sub-constraints to be applied to each of the regions.

The dividing of the detected boundary may include calculating a distance between the detected boundary and an annotation marked by the user feedback, and based on the calculated distance, dividing the detected boundary into the boundary to be fixed and the boundary to be modified.

The dividing of an image may include dividing the image by determining that a region including the boundary to be fixed is a region to be fixed, that a region including the annotation marked by the user feedback is a region to be unconditionally modified, and that the remainder of the image is a region to be conditionally modified.

The generating the constraint may further include generating a first sub-constraint for the region to be fixed, a second sub-constraint for the region to be unconditionally modified, and a third sub-constraint for the region to be conditionally modified. Additionally, the modifying the detected boundary may include modifying a first portion of the detected boundary within the region to be fixed by applying the first sub-constraint to the image segmentation process, a second portion of the detected boundary within the region to be unconditionally modified by applying the second sub-constraint to the image segmentation process, and a third portion of the detected boundary within the region to be conditionally modified by applying the third sub-constraint to the image segmentation process.

The dividing of the detected boundary may further include calculating a distance between the detected boundary and an annotation marked by the user feedback, and determining that N % of the detected boundary closest to the annotation is the boundary to be modified and the remainder of the detected boundary is the boundary to be fixed.

N may be a constant that has been set in advance according to performance or usage of an image segmenting apparatus, or may be a variable that depends on a context of the user feedback.

Other features and aspects will be apparent from the following detailed description, the drawings, and the claims.

BRIEF DESCRIPTION OF THE DRAWINGS

FIGS. 4A to 4D are diagrams illustrating examples of information received to expand a boundary.

FIGS. 5A to 5D are diagrams illustrating examples of information received to reduce a boundary.

Throughout the drawings and the detailed description the same reference numerals refer to the same elements. The drawings may not be to scale, and the relative size, proportions, and depiction of elements in the drawings may be exaggerated for clarity, illustration, and convenience.

DETAILED DESCRIPTION

The following description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Image segmentation processes may be classified into boundary-based image segmentation process and region-based image segmentation process. Boundary-based image segmentation process is a process or method that recognizes pixels with different intensities from those of peripheral pixels as a boundary or contour, and segments an image based on the boundary or contour. Region-based image segmentation process is an algorithm that segments an image by grouping pixels with identical characteristics (e.g., brightness, color, etc.) as one region. Examples of boundary-based image segmentation include Active Contour Models and Level Set, and examples of region-based image segmentation include Graph Cuts.

Hereinafter, an image segmenting apparatus according to an embodiment is described in detail with reference to FIG. 1.

Figure 1:
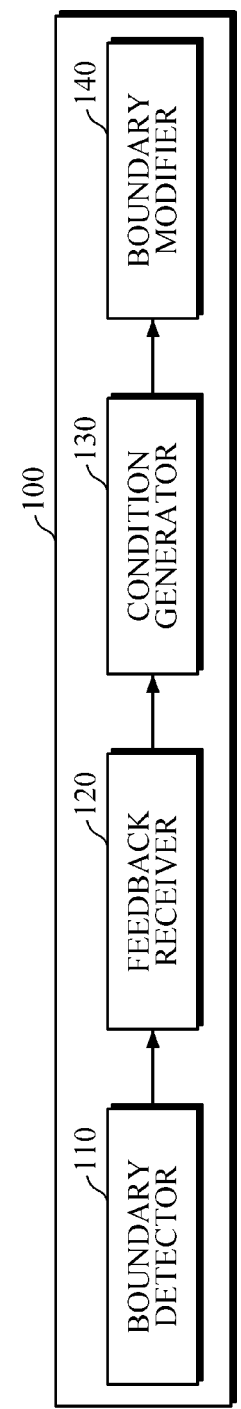
FIG. 1 is a block diagram illustrating an example of an image segmenting apparatus, in accordance with an embodiment.

FIG. 1 is a block diagram illustrating an example of an image segmenting apparatus, in accordance with an embodiment.

Referring to FIG. 1, an image segmenting apparatus 100 includes a boundary detector 110, a feedback receiver 120, a condition generator 130, and a boundary modifier 140.

The boundary detector 110 detects a boundary or a contour from an image using an image segmentation process, and segments the image based on the detected boundary or contour. The boundary detector 110 uses various image segmentation processes. In one example, a level-set process may be used among the various image segmentation processes.

The level-set process is a mathematical method to detect a boundary or contour by evolving a curve represented as a level set.

In the level-set process, contour (C) may be represented by Equation 1 below:

$$C=\{(x,y)|\emptyset(x,y)=0\} \quad \text{[Equation 1]}$$

In this case, Ø denotes a level set function and the contour (C) is represented as the zero level set of Ø. Ø may take positive values inside contour (C), and negative values outside the contour (C).

In addition, the evolution equation of the level set function (Ø) at a speed (F) is represented by Equation 2 below:

$$\frac{\partial \phi}{\partial t} = |\nabla \phi| F, \phi(0, x, y) = \phi_0(x, y) \quad \text{[Equation 2]}$$

In this case, t denotes time.

In addition, an initial contour is represented by Equation 3 below:

$$\{(x,y)|\emptyset_0(x,y)=0\} \quad \text{[Equation 3]}$$

That is, the boundary detector 110 detects a boundary or contour by evolving the contour (C) (Equation 1) having an initial contour (Equation 3) toward a normal at speed (F) using the evolution Equation (Equation 2).

The feedback receiver 120 receives information, such as a user feedback, information from an internal preset processor, or information from an input processor, on the boundary detected by the boundary detector 110. For example, the feedback receiver 120 receives information, such as a user feedback, that indicates an area to be modified in a space inside or outside the boundary.

According to an embodiment, a user feedback may be a boundary expanding feedback or a boundary reducing feedback.

The boundary expanding feedback may include marking a dot or line outside the boundary, drawing a line starting and ending inside the boundary and passing outside the boundary, or drawing a line starting inside the boundary and ending outside the boundary.

On the other hand, the boundary reducing feedback includes marking a dot or line inside the boundary, drawing a line starting and ending outside the boundary and passing inside the boundary, or drawing a line starting outside the boundary but ending inside the boundary.

The feedback receiver 120 receives a user feedback using various input means, including a mouse, a trackball, a keyboard, a touch screen, and the like.

The condition generator 130 generates a constraint of the image segmentation process according to a received user feedback. For example, the condition generator 130 analyzes a user feedback to determine whether the user feedback is a feedback for expanding the boundary (hereinafter, referred to as a boundary expanding feedback) or a feedback for reducing the boundary (hereinafter, referred to as a boundary reducing feedback), and generates a constraint according to the result of the analysis. In addition, based on the user feedback, the condition generator 130 divides an image into a region to be fixed, a region to be unconditionally modified, and a region to be conditionally modified, and generate a constraint to be applied to each region.

The condition generator 130 is described in detail with reference to FIG. 2.

The boundary modifier 140 modifies a boundary detected by the boundary detector 110, by applying the generated constraint to the image segmentation process.

Hereinafter, detailed description about the condition generator 130 is provided with reference to FIG. 2.

Figure 2:
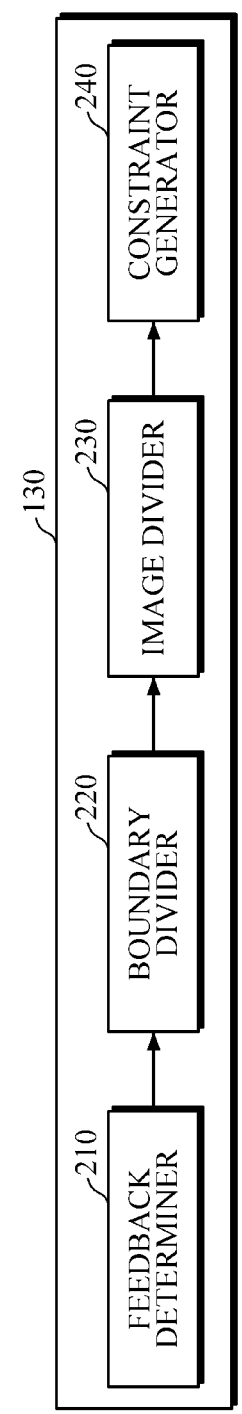
FIG. 2 is a diagram illustrating a condition generator shown in FIG. 1, in accordance with an embodiment.

FIG. 2 is a diagram illustrating the condition generator 130 shown in FIG. 1, in accordance with an embodiment.

Referring to FIG. 2, the condition generator 130 includes a feedback determiner 210, a boundary divider 220, an image divider 230, and a constraint generator 240.

The feedback determiner 210 may analyze a user feedback received from feedback receiver 120 to determine whether the user feedback aims to expand or reduce a boundary.

The feedback determiner 210 may analyze the feedback to determine characteristics of a user feedback (e.g., a location and range of each annotation made by the user, and a shape of each annotation), and determine, based on a result of the determined characteristics, whether the user feedback aims to expand or reduce a boundary.

For example, if the user feedback is one of marking a dot outside the boundary, drawing a line outside the boundary, drawing a line starting and ending inside the boundary and passing outside the boundary, or drawing a line starting inside the boundary and ending outside the boundary, the feedback determiner 210 determines the user feedback to be a boundary expanding feedback. If the user feedback is one of marking a dot inside of the boundary, drawing a line inside the boundary, drawing a line starting and ending outside the boundary and passing inside the boundary, or drawing a line starting outside the boundary and ending inside the boundary, the feedback determiner 210 determines the user feedback to be a boundary reducing feedback.

Based on the user feedback determined by the feedback determiner 210, the boundary divider 220 may divide the boundary detected by the boundary detector 110 into a boundary to be fixed and a boundary to be modified.

In one aspect, the boundary divider 220 calculates a distance between the boundary and an annotation made via the user feedback. Then, according to the calculated distance, the boundary divider 220 divides the boundary by determining that N % of the boundary, which is a portion of the boundary closest to the annotation, is a boundary to be modified, and the rest of the boundary is a boundary to be fixed. In this case, N may be a constant that has been set in advance by a user according to performance or usage of a system, or may be a variable depending on feedback context (e.g., a range of an annotation made by the user).

The boundary divider 220 calculates a distance between the boundary and an annotation made via the user feedback using various distance measuring functions, such as Euclidean distance, Mahalanobis distance, and the like.

The image divider 230 divides an image into a region to be fixed, a region to be unconditionally modified, and a region to be conditionally modified, and generate a constraint for each region.

The image divider 230 divides an image by determining that a region within a preset range with respect to a boundary to be fixed is a region to be fixed, that a region within a preset range around an annotation made by a user is a region to be unconditionally modified, and that the remainder of the image is a region to be conditionally modified. According to an embodiment, the region to be unconditionally modified includes a region on the shortest path from the annotation made by the user to the boundary.

The constraint generator 240 generates a constraint for each region (a region to be fixed, a region to be unconditionally modified, and a region to be conditionally modified). For example, if the image segmentation process is a level set process, the constraint generator 240 generates a level set constraint related to speed (F) (see Equation 2).

If speed (F) in a specific region is 0 in the level set process (see Equation 2), a boundary within the specific region is to be fixed. If speed (F) in a specific region is a negative number, a boundary within the specific region is to be expanded. If speed (F) in a specific region is a positive number, a boundary within the specific region is to be reduced.

Thus, the constraint generator 240 generates different constraints depending on a result of the determination made by the feedback determiner 210.

For example, if the feedback determiner 210 determines that a user feedback is a boundary expanding feedback, the constraint generator 240 generates constraints (F') for each region as follows:

Region to be fixed: F'=0
Region to be unconditionally fixed: F'=−A
Region to be conditionally fixed: F'=min(0, F)

In this case, A is a positive number, which may be previously set by a user or may be set to be a value whose absolute value is the biggest among F values obtained in all the portions of the boundary.

Alternatively, if the feedback determiner 210 determines that a user feedback is a boundary reducing feedback, the constraint generator 240 generates constraints (F') for each region as follows:

Region to be fixed: F'=0
Region to be unconditionally fixed: F'=A
Region to be conditionally fixed: F'=max(0, F)

In this case, A is a positive number, which may be previously set by a user or may be set to be a value whose absolute value is the biggest among F values obtained in all the regions of the boundary. Meanwhile, a boundary modifier (such as the boundary modifier 140 of FIG. 1) may modify the boundary by applying the generated constraint to the image segmentation process.

For example, if the image segmentation process is a level set process, the boundary segmentation by the boundary modifier 140 may reflect the constraint F' of each region (a region to be fixed, a region to be unconditionally fixed, and a region to be conditionally fixed) generated by the constraint generator 240 in the level set process, by substituting the constraint F' for the speed (F) in Equation 2. In addition, the boundary modifier 140 may redetect a boundary in each region using the level set process in which the corresponding constraint F' has been reflected.

In a first example, a user feedback is a boundary expanding feedback. The boundary of a region to be fixed is not changed. However, the boundary of a region to be unconditionally modified is expanded so that the region to be unconditionally modified is situated inside the boundary, while the boundary of a region to be conditionally modified is expanded conditionally, so that a portion of the region to be conditionally modified is situated inside of the boundary and the remaining portion thereof remains outside the boundary.

In another example, the user feedback is a boundary reducing feedback. The boundary of a region to be fixed is not changed. However, the boundary of a region to be unconditionally modified is reduced so that the region to be unconditionally modified is situated outside the boundary, while the boundary of a region to be conditionally modified is reduced conditionally so that a portion of the region to be conditionally modified is situated outside the boundary and the remaining portion thereof remains inside the boundary.

Figure 3:
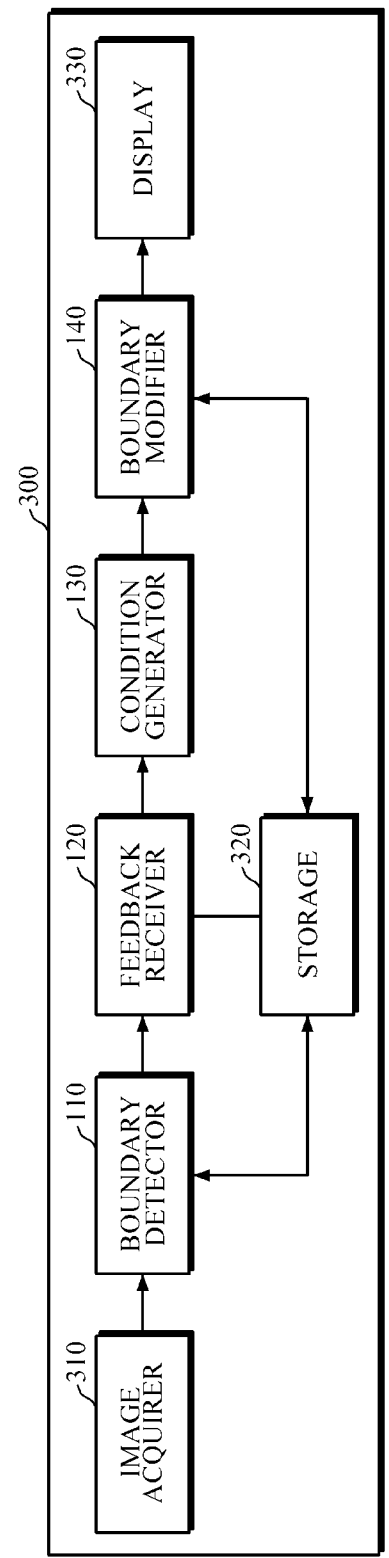
FIG. 3 is a diagram illustrating another example of an image segmenting apparatus, in accordance with an embodiment.
Figure 4A:
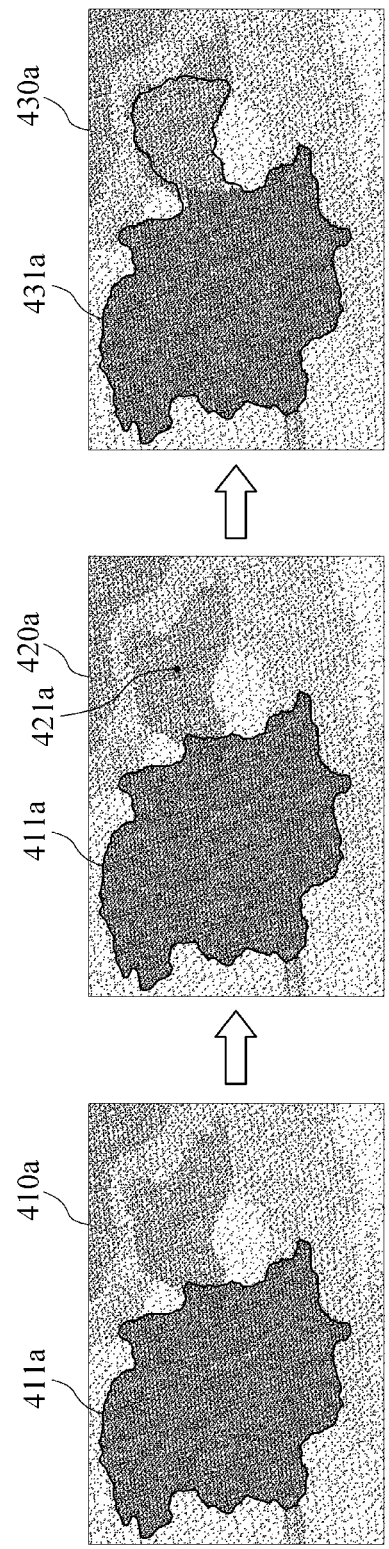
Figure 4B:
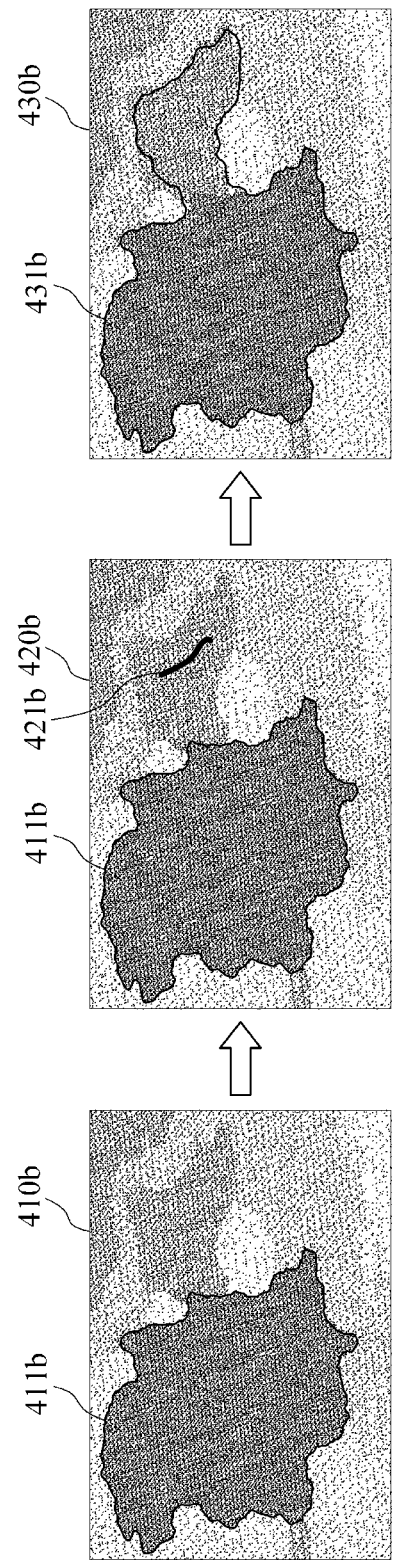
Figure 5A:
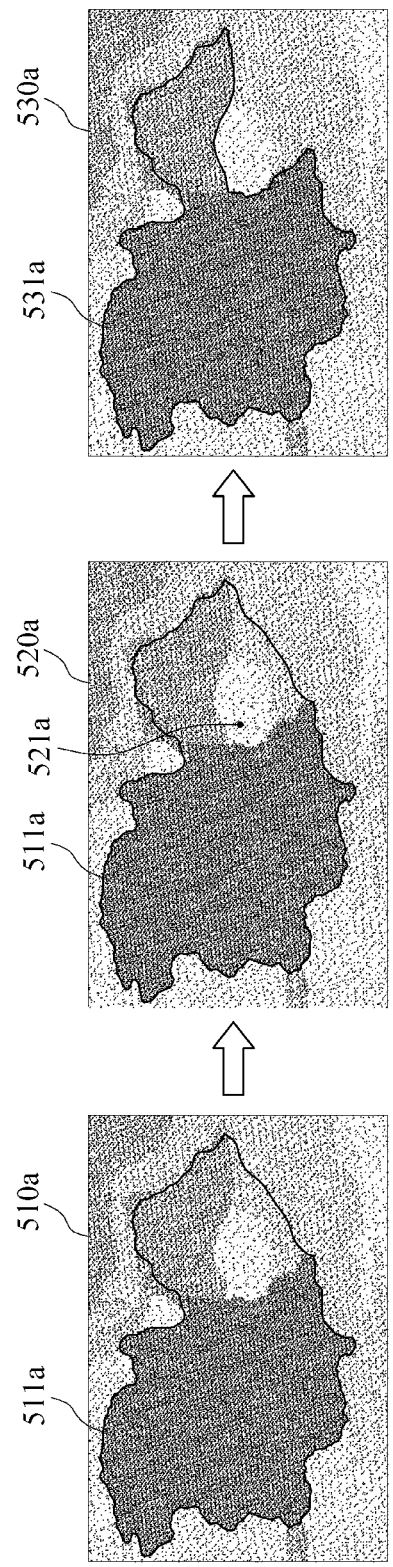
Figure 5B:
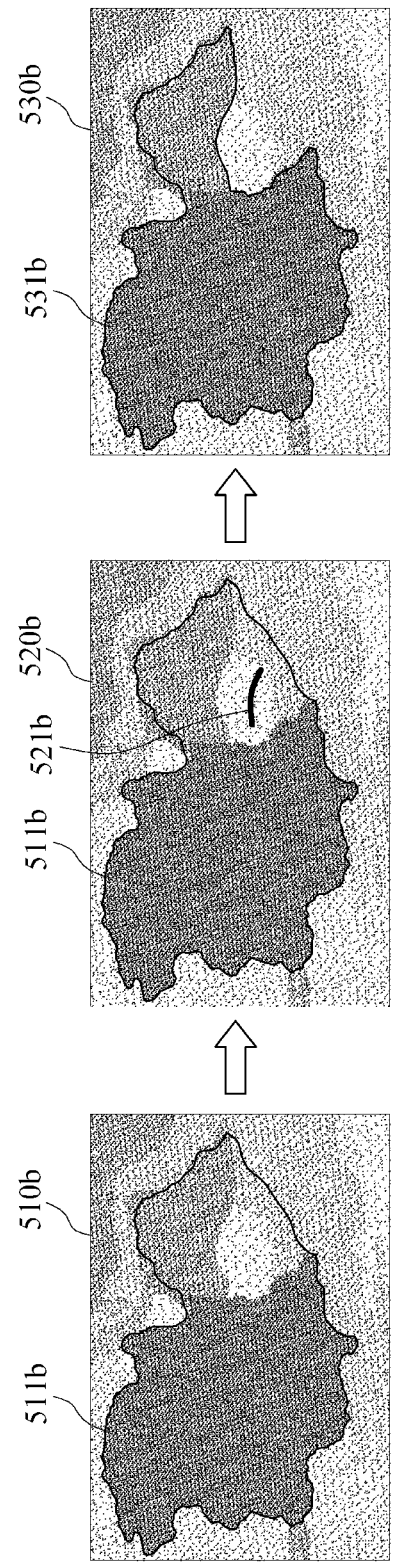
Figure 5D:
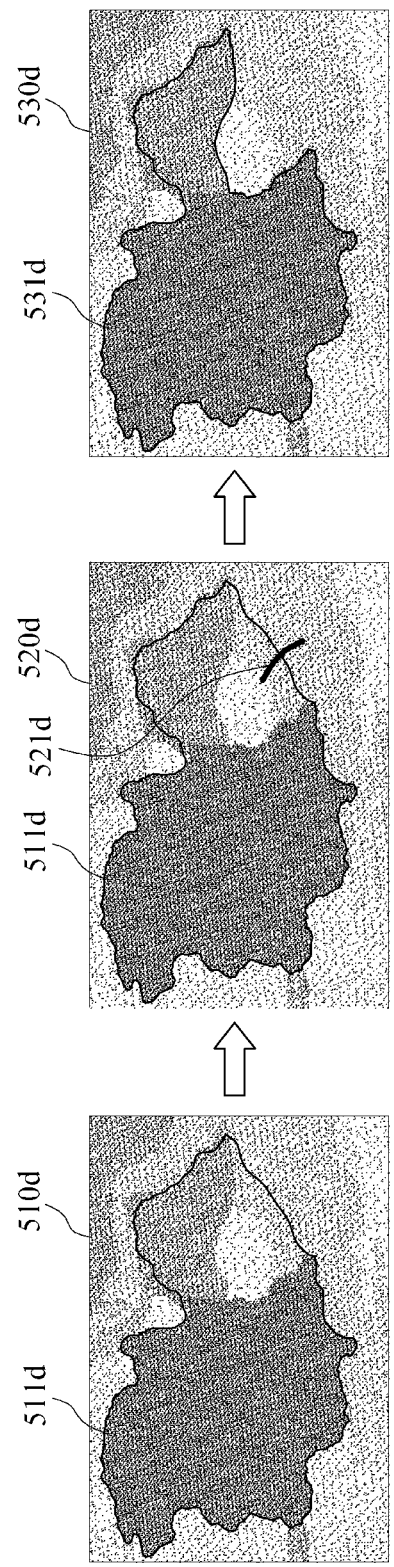

FIG. 3 is a block diagram illustrating another example of an image segmenting apparatus, in accordance with an embodiment.

Referring to FIG. 3, an image segmenting apparatus 300 further includes an image acquirer 310, a storage 320, and a display 330, in addition to structural components 110-140 described above with respect to the image segmenting apparatus 100 shown in FIG. 1. A person of ordinary skill in the relevant art will appreciate that the various structural components included in the image segmenting apparatus 300 may be configured to be embodied in a single processor component, which would be configured to perform each function of the various structural components.

The image acquirer 310 acquires an image. The image may be one of various medical images including Computed Radiography (CR) images, Computed Tomography (CT) images, ultrasonic images, Magnetic Resonance Imaging (MRI) images.

The storage 320 stores an image acquired by the image acquirer 310, a boundary detection result obtained by the boundary detector 110, and/or a boundary modification result obtained by the boundary modifier 140.

The storage 320 may include a flash memory, a hard disk type, a multimedia card micro, a card-type memory (e.g., an SD or XD memory), Random Access Memory (RAM), Static Random Access Memory (SRAM), Read Only Memory (ROM), Electrically Erasable Programmable Read Only Memory (EEPROM), Programmable Read Only Memory (PROM), a magnetic memory, a magnetic disk, or an optical disk.

The display 330 visually outputs information processed in the image segmenting apparatus 300. The display 330 visually outputs a boundary detection result and a boundary modification result.

The display 330 may include a liquid crystal display, a thin film transistor liquid crystal display, an organic light emitting diode, a flexible display, a 3D display, a glass-type display (e.g., Head Mounted Display (HMD), Face Mounted Display (FMD), Eye Mounted Display (EMD), Eye Glass Display (EGD)), or the like.

The display 330 may be a touch screen layered with a touch pad. In this case, the display 330 may be used not just as an output device, but as an input device.

FIGS. 4A to 4D are diagrams illustrating examples of user feedback to expand a boundary, in accordance with an embodiment. In one example, it is assumed that the user feedback is input through a touch screen.

The left images 410a, 410b, 410c, and 410d in FIGS. 4A to 4D, respectively, are images representing a boundary detection result obtained by the boundary detector 110. The middle images 420a, 420b, 420c, and 420d in FIGS. 4A to 4D, respectively, are images in which a user feedback is input. The right images 430a, 430b, 430c, and 430d in FIGS. 4A to 4D, respectively, are images in which a boundary is modified by the boundary modifier 140 based on the user feedback.

First, the boundary detector 110 detects a boundary 411a, 411b, 411c, or 411d from an original image using an image segmentation process. At this point, a region that should be inside the boundary 411a, 411b, 411c, or 411d may be outside the boundary 411a, 411b, 411c, or 411d. In such a case, a user expands the boundary 411a, 411b, 411c, or 411d through feedback.

That is, if the feedback receiver 120 receives a feedback 421a of marking a dot outside the boundary 411a, 411b, 411c, or 411d (see FIG. 4A), a feedback 421b of drawing a line outside the boundary 411a, 411b, 411c, or 411d (see FIG. 4B), a feedback 421c of drawing a line starting and ending inside the boundary 411a, 411b, 411c, or 411d and passing outside the boundary 411a, 411b, 411c, or 411d (see FIG. 4C), or a feedback 421d of drawing a line starting inside the boundary 411a, 411b, 411c, or 411d but ending outside the boundary 411a, 411b, 411c, or 411d (see FIG. 4D), the condition generator 130 determines the feedback 421a, 421b, 421c, or the 421d to be a boundary expanding feedback. The boundary modifier 140 then redetects a new boundary 431a, 431b, 431c, or 431d reflecting the feedback 421a, 421b, 421c, or 421d.

FIGS. 5A to 5D are diagrams illustrating examples of user feedback for reducing a boundary, in accordance with an embodiment.

The left images 510a, 510b, 510c, and 510d in FIGS. 5A to 5D, respectively, are images representing a boundary detection result obtained by the boundary detector 110. The middle images 520a, 520b, 520c, and 520d in FIGS. 5A to 5D, respectively, are images in which a user feedback is input. The right images 530a, 530b, 530c, and 530d in FIGS. 5A to 5D, respectively, are images in which a boundary is modified by the boundary modifier 140 based on the user feedback.

First, the boundary detector 110 detects a boundary 511a, 511b, 511c, or 511d from an original image using an image segmentation process. At this point, a region that should be outside the boundary 511a, 511b, 511c, or 511d may be inside the boundary 511a, 511b, 511c, or 511d. In such a case, a user may reduce the boundary 511a, 511b, 511c, or 511d through feedback.

That is, if the feedback receiver 120 receives a feedback 521a of marking a dot inside the boundary 511a, 511b, 511c, or 511d (see FIG. 5A), a feedback 521b of drawing a line inside the boundary 511a, 511b, 511c, or 511d (see FIG. 5B), a feedback 521c of drawing a line starting and ending outside the boundary 511a, 511b, 511c, or 511d and passing inside the boundary 511a, 511b, 511c, or 511d (see FIG. 5C), or a feedback 521d of drawing a line starting outside the boundary 511a, 511b, 511c, or 511d but ending inside the boundary 511a, 511b, 511c, or 511d (see FIG. 5D), the condition generator 130 may determine the feedback 521a, 521b, 521c, or 521d to be a boundary reducing feedback. The boundary modifier 140 may then redetect a new boundary 531a, 531b, 531c, or 531d reflecting the feedback 521a, 521b, 521c, or 521d.

Figure 6:
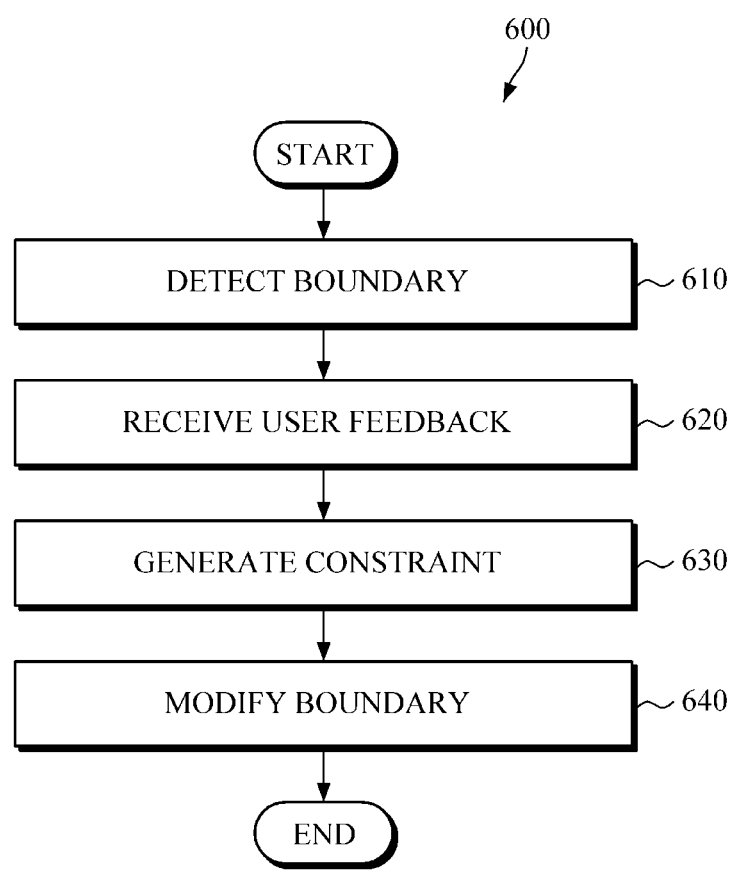
FIG. 6 is a flowchart illustrating an example of an image segmenting method, in accordance with an embodiment.

FIG. 6 is a flowchart illustrating an example of an image segmenting method, in accordance with an embodiment.

Referring to FIG. 6, an image segmenting method 600 starts out by detecting a boundary from an image using an image segmentation process in operation 610. For example, the image segmenting apparatus 100 or 300 detects a boundary or contour from an image using a level set process.

Then, a feedback on the detected boundary is received from a user in operation 620. For example, the image segmenting apparatus 100 or 300 may receive a feedback that aims to select a region placed inside or outside the boundary for a purpose of modification.

The feedback may be classified into a boundary expanding feedback or a boundary reducing feedback. The boundary expanding feedback may be marking a dot or line outside the boundary, drawing a line starting and ending inside the boundary and passing outside the boundary, or drawing a line starting inside the boundary but ending outside the boundary. Alternatively, the boundary reducing feedback may be marking a dot or line inside the boundary, drawing a line starting and ending outside the boundary and passing inside the boundary, or drawing a line starting outside the boundary but ending inside the boundary.

Then, the feedback is analyzed and a constraint of the image segmentation process is generated in operation 630. For example, the image segmenting apparatus 100 or 300 analyzes a feedback from a user and generates a level set constraint related to speed (F).

Then, the boundary is modified by applying the generated constraint to the image segmentation process in operation 640. For example, the image segmenting apparatus 100 or 300 may reflect the constraints in the image segmentation process by substituting the constraint for speed (F) in Equation 2, and modifying the boundary using a level set reflecting the constraint.

Figure 7:
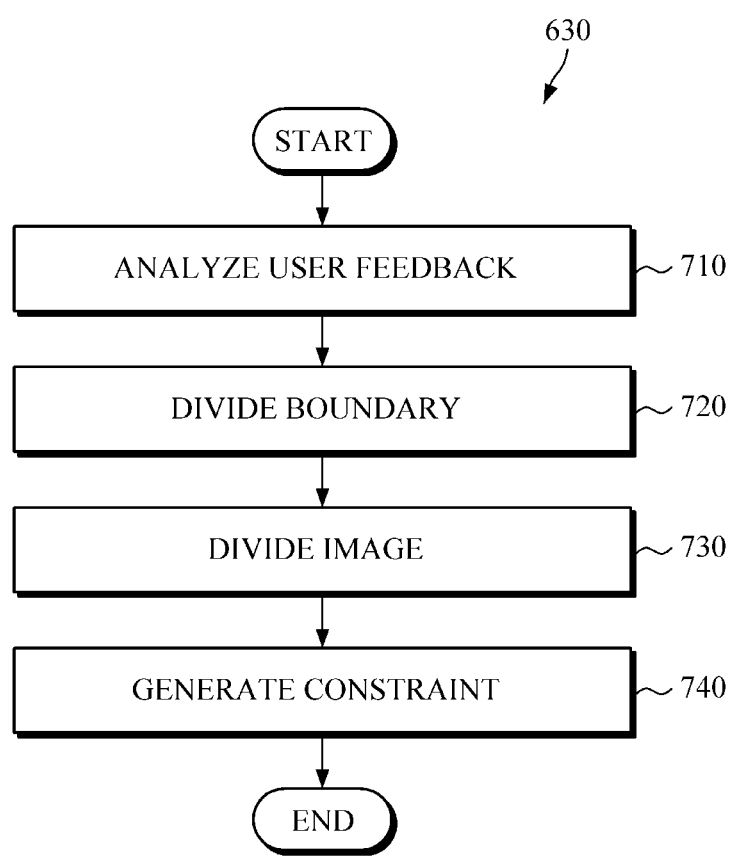
FIG. 7 is a flowchart illustrating a constraint generating operation of FIG. 6, in accordance with an embodiment.

FIG. 7 is a flowchart illustrating the constraint generating operation 630 shown in FIG. 6, in accordance with an embodiment.

Referring to FIG. 7, the constraint generating operation 630 shown in FIG. 6 starts out by analyzing a user feedback to determine whether the feedback is a boundary expanding feedback or a boundary reducing feedback in operation 710. For example, the image segmenting apparatus 100 or 300 may analyze a feedback to determine characteristics of a user feedback (e.g., a location and range of each annotation made via the feedback, and a shape of each annotation), and determine, based on the determined characteristics, whether the feedback is a boundary expanding feedback or a boundary reducing feedback.

For example, if the feedback is one of marking a dot outside the boundary, drawing a line outside the boundary, drawing a line starting and ending inside the boundary and passing outside the boundary, or drawing a line starting inside the boundary and ending outside the boundary, the image segmenting apparatus 100 or 300 determines the feedback to be a boundary expanding feedback. Alternatively, if the feedback is one of marking a dot inside the boundary, drawing a line inside the boundary, drawing a line starting and ending outside the boundary and passing inside the boundary, or drawing a line starting outside the boundary and ending inside the boundary, the image segmenting apparatus 100 or 300 determines the feedback to be a boundary reducing feedback.

Based on the feedback, the boundary is then divided into a boundary to be fixed and a boundary to be modified in operation 720. For example, the image segmenting apparatus 100 or 300 may calculate a distance between a boundary and an annotation marked via the feedback and divide the boundary according to the calculated distance, by determining that N % of the boundary, which is a portion of the boundary closest to the annotation, is a boundary to be modified, and the rest of the boundary is a boundary to be fixed. In this case, N may be a constant previously set by a user according to performance or usage of a system, or a variable that depends on feedback context (e.g., a range of an annotation made by the feedback, or the like).

Then, based on the division of the boundary, the image is divided into a region to be fixed, a region to be unconditionally modified, and a region to be conditionally modified in operation 730. For example, the image segmenting apparatus 100 or 300 may determine that a region within a preset range of a boundary to be fixed is a region to be fixed, a region within a preset range around the annotation made via the feedback is a region to be unconditionally modified, and the remainder of the image is a region to be conditionally modified.

In operation 740, a constraint for the image segmentation process is generated for each region (a region to be fixed, a region to be unconditionally modified, and a region to be conditionally modified). For example, if the image segmentation process is a level set process, the image segmenting apparatus 100 or 300 may generate a level set constraint (F') related to speed (F) for each region (see Equation 2).

According to an exemplary embodiment, if a feedback is a boundary expanding feedback, the image segmenting apparatus 100 or 300 generates constraints (F') as follows:
Region to be fixed: F'=0
Region to be unconditionally modified: F'=−A
Region to be conditionally modified: F'=min(0, F)

According to another exemplary embodiment, if a user feedback is a boundary reducing feedback, the image segmenting apparatus 100 or 300 generates constraints (F') as follows:
Region to be fixed: F'=0
Region to be unconditionally modified: F'=A
Region to be conditionally modified: F'=max(0, F)

In one example, A is a positive number, and may be set in advance by a user or may be set to be a value whose absolute value is the biggest among F values obtained in all the region of the boundary.

The boundary detector, feedback receiver, condition generator, boundary modifier, feedback determiner, boundary divider, image divider, constraint generator, image acquirer, and storage illustrated in FIGS. 1-3 that perform the operations described herein with respect to FIGS. 6-7 are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 6-7. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 6-7 that perform the operations described herein are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose processes for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A medical image segmenting apparatus, comprising:
a memory configured to store instructions; and
at least one processor,
wherein the at least one processor, when executing the stored instructions, is configured to:
detect a boundary from a medical image using an image segmentation process,
receive a user's input providing feedback information on the detected boundary,
determine whether the feedback information comprises a boundary expanding feedback or a boundary reducing feedback by analyzing the received user's input,
divide, based on the feedback information, the detected boundary into a boundary to be fixed and a boundary to be modified,
divide, based on the division of the detected boundary, the medical image into a region to be fixed, a region to be unconditionally modified, and a region to be conditionally modified,
generate a constraint for the image segmentation process based on a result of the determination, and
modify the detected boundary by applying the generated constraint to the image segmentation process,
wherein the constraint comprises sub-constraints to be applied to each of the regions, and
wherein the at least one processor, when executing the stored instructions, is further configured to:
calculate a distance between the detected boundary and an annotation marked by the user feedback, and
divide, based on the calculated distance, the detected boundary into the boundary to be fixed and the boundary to be modified.

2. The medical image segmenting apparatus of claim 1, wherein the image segmentation process comprises a level set process.

3. The medical image segmenting apparatus of claim 1, wherein the at least one processor, when executing the stored instructions, is further configured to:
determine that the feedback information comprises the boundary expanding feedback when the feedback information comprises one of marking a dot outside the detected boundary, drawing a line outside the detected boundary, drawing a line starting and ending inside the detected boundary and passing outside the detected boundary, or drawing a line starting inside the detected boundary but ending outside the detected boundary, and
determine that the feedback information comprises the boundary reducing feedback when the feedback information comprises one of marking a dot inside the detected boundary, drawing a line inside the detected boundary, drawing a line starting and ending outside the detected boundary and passing inside the detected boundary, or drawing a line starting outside the detected boundary but ending inside the detected boundary.

4. The medical image segmenting apparatus of claim 1, wherein the at least one processor, when executing the stored instructions, is further configured to:
divide the medical image by determining that:
a region including the boundary to be fixed is the region to be fixed,
a region including the annotation marked by the user feedback is the region to be unconditionally modified, and
the remainder of the medical image is the region to be conditionally modified.

5. The medical image segmenting apparatus of claim 4, wherein the at least one processor, when executing the stored instructions, is further configured to:
generate a first sub-constraint for the region to be fixed, a second sub-constraint for the region to be unconditionally modified, and a third sub-constraint for the region to be conditionally modified,
modify a first portion of the detected boundary within the region to be fixed by applying the first sub-constraint to the image segmentation process,
modify a second portion of the detected boundary within the region to be unconditionally modified by applying the second sub-constraint to the image segmentation process, and
modify a third portion of the detected boundary within the region to be conditionally modified by applying the third sub-constraint to the image segmentation process.

6. The medical image segmenting apparatus of claim 1, wherein the at least one processor, when executing the stored instructions, is further configured to:
calculate a distance between the detected boundary and an annotation marked by the user feedback, and
determine a percentage of the detected boundary closest to the annotation as the boundary to be modified and the remainder of the detected boundary as the boundary to be fixed.

7. The medical image segmenting apparatus of claim 6, wherein the percentage of the detected boundary closest to the annotation is determined based on at least one of:
a constant that has been set in advance according to performance or usage of the medical image segmenting apparatus, or
a variable that depends on a context of the user feedback.

8. A computer program product comprising a non-transitory computer readable storage medium having a computer readable program stored therein, wherein the computer readable program, when executed by a computing device, causes the computing device to:
detect a boundary from a medical image using an image segmentation process;
receive feedback information about the detected boundary input by a user;
determine whether the feedback information comprises a boundary expanding feedback or a boundary reducing feedback by analyzing the received feedback information;
divide, based on the feedback information, the detected boundary into a boundary to be fixed and a boundary to be modified;
divide, based on the division of the detected boundary, the medical image into a region to be fixed, a region to be unconditionally modified, and a region to be conditionally modified;
generate a constraint for the image segmentation process based on a result of the determination; and
modify the detected boundary by applying the generated constraint to the image segmentation process,
wherein the constraint comprises sub-constraints to be applied to each of the regions, and wherein the computer readable program, when executed by the computing device, further causes the computing device to:
calculate a distance between the detected boundary and an annotation marked by the user feedback, and
based on the calculated distance, divide the detected boundary into the boundary to be fixed and the boundary to be modified.

9. The computer program product of claim 8, wherein the image segmentation process comprises a level set process.

10. The computer program product of claim 8, wherein the computer readable program, when executed by the computing device, further causes the computing device to:
determine that the feedback information comprises the boundary expanding feedback when the feedback information comprises one of marking a dot outside the detected boundary, drawing a line outside the detected boundary, drawing a line starting and ending inside the detected boundary and passing outside the detected boundary, or drawing a line starting inside the detected boundary but ending outside the detected boundary, and
determine that the feedback information comprises the boundary reducing feedback when the feedback information comprises one of marking a dot inside the detected boundary, drawing a line in the detected boundary, drawing a line starting and ending outside the detected boundary and passing inside the detected boundary, or drawing a line starting outside the detected boundary but ending inside the detected boundary.

11. The computer program product of claim 8, wherein the computer readable program, when executed by the computing device, further causes the computing device to:
divide the medical image by determining that:
a region including the boundary to be fixed is the region to be fixed,
a region including the annotation marked by the user feedback is the region to be unconditionally modified, and
the remainder of the medical image is the region to be conditionally modified.

12. The computer program product of claim 11, wherein the computer readable program, when executed by the computing device, further causes the computing device to:
generate a first sub-constraint for the region to be fixed, a second sub-constraint for the region to be unconditionally modified, and a third sub-constraint for the region to be conditionally modified,
modify a first portion of the detected boundary within the region to be fixed by applying the first sub-constraint to the image segmentation process,
modify a second portion of the detected boundary within the region to be unconditionally modified by applying the second sub-constraint to the image segmentation process, and
modify a third portion of the detected boundary within the region to be conditionally modified by applying the third sub-constraint to the image segmentation process.

13. The computer program product of claim 8, wherein the computer readable program, when executed by the computing device, further causes the computing device to:
calculate a distance between the detected boundary and an annotation marked by the user feedback, and
determine a percentage of the detected boundary closest to the annotation as the boundary to be modified and the remainder of the detected boundary as the boundary to be fixed.

14. The computer program product of claim 13, wherein the percentage of the detected boundary closest to the annotation is determined based on at least one of:
a constant that has been set in advance according to performance or usage of a medical image segmenting apparatus, or
a variable that depends on a context of the user feedback.

15. A medical image segmenting apparatus, comprising:
a memory configured to store instructions; and
at least one processor,
wherein the at least one processor, when executing the stored instructions, is configured to:
detect a boundary from a medical image using an image segmentation process,
receive feedback information about the detected boundary input by a user,
determine whether the feedback information comprises a boundary expanding feedback or a boundary reducing feedback by analyzing the feedback information,
divide, based on the feedback information, the detected boundary into a boundary to be fixed and a boundary to be modified,
divide, based on the division of the detected boundary, the medical image into a region to be fixed, a region to be unconditionally modified, and a region to be conditionally modified,
modify the detected boundary by applying a constraint based on the determined feedback information to the image segmentation process, and
wherein the constraint comprises sub-constraints to be applied to each of the regions, and
wherein the at least one processor, when executing the stored instructions, is further configured to:
calculate a distance between the detected boundary and an annotation marked by the user feedback, and
divide, based on the calculated distance, the detected boundary into the boundary to be fixed and the boundary to be modified.

16. The medical image segmenting apparatus of claim 15, wherein the at least one processor, when executing the stored instruction, is further configured to:
determine a speed of at least one region of the detected boundary to be modified using a predetermined equation.

17. The medical image segmenting apparatus of claim 15, wherein the at least one processor, when executing the stored instruction, is further configured to:
determine that the feedback information comprises the boundary expanding feedback when the feedback information comprises one of marking a dot outside the detected boundary, drawing a line outside the detected boundary, drawing a line starting and ending inside the detected boundary and passing outside the detected boundary, or drawing a line starting inside the detected boundary but ending outside the detected boundary, and
determine that the feedback information comprises the boundary reducing feedback when the feedback information comprises one of marking a dot inside the detected boundary, drawing a line inside the detected boundary, drawing a line starting and ending outside the detected boundary and passing inside the detected boundary, or drawing a line starting outside the detected boundary but ending inside the detected boundary.

18. A computer program product comprising a non-transitory computer readable storage medium having a computer readable program stored therein, wherein the computer readable program, when executed by a computing device, causes the computing device to:

detect a boundary from a medical image using an image segmentation process;

receive feedback information about the detected boundary input by a user;

determine whether the feedback information comprises a boundary expanding feedback or a boundary reducing feedback by analyzing the received feedback information;

divide, based on the feedback information, the detected boundary into a boundary to be fixed and a boundary to be modified;

based on the division of the detected boundary, divide the medical image into a region to be fixed, a region to be unconditionally modified, and a region to be conditionally modified; and modify the detected boundary by applying a constraint based on the determined feedback information to the image segmentation process, wherein the constraint comprises sub-constraints to be applied to the entirety of each of the regions, and wherein the computer readable program, when executed by the computing device, further causes the computing device to:

calculate a distance between the detected boundary and an annotation marked by the user feedback, and based on the calculated distance, divide the detected boundary into the boundary to be fixed and the boundary to be modified.

19. The computer program product of claim 18, wherein the computer readable program, when executed by the computing device, further causes the computing device to:

determine a speed of at least one region of the detected boundary to be modified using a predetermined equation.

20. The computer program product of claim 18, wherein the computer readable program, when executed by the computing device, further causes the computing device to:

determine that the feedback information comprises the boundary expanding feedback when the feedback information comprises one of marking a dot outside the detected boundary, drawing a line outside the detected boundary, drawing a line starting and ending inside the detected boundary and passing outside the detected boundary, or drawing a line starting inside the detected boundary but ending outside the detected boundary, and determine that the feedback information comprises the boundary reducing feedback when the feedback information comprises one of marking a dot inside the detected boundary, drawing a line in the detected boundary, drawing a line starting and ending outside the detected boundary and passing inside the detected boundary, or drawing a line starting outside the detected boundary but ending inside the detected boundary.

* * * * *